Jan. 30, 1962 E. S. BOERNER Plant Pat. 2,126
CHRYSANTHEMUM PLANT
Filed March 17, 1961
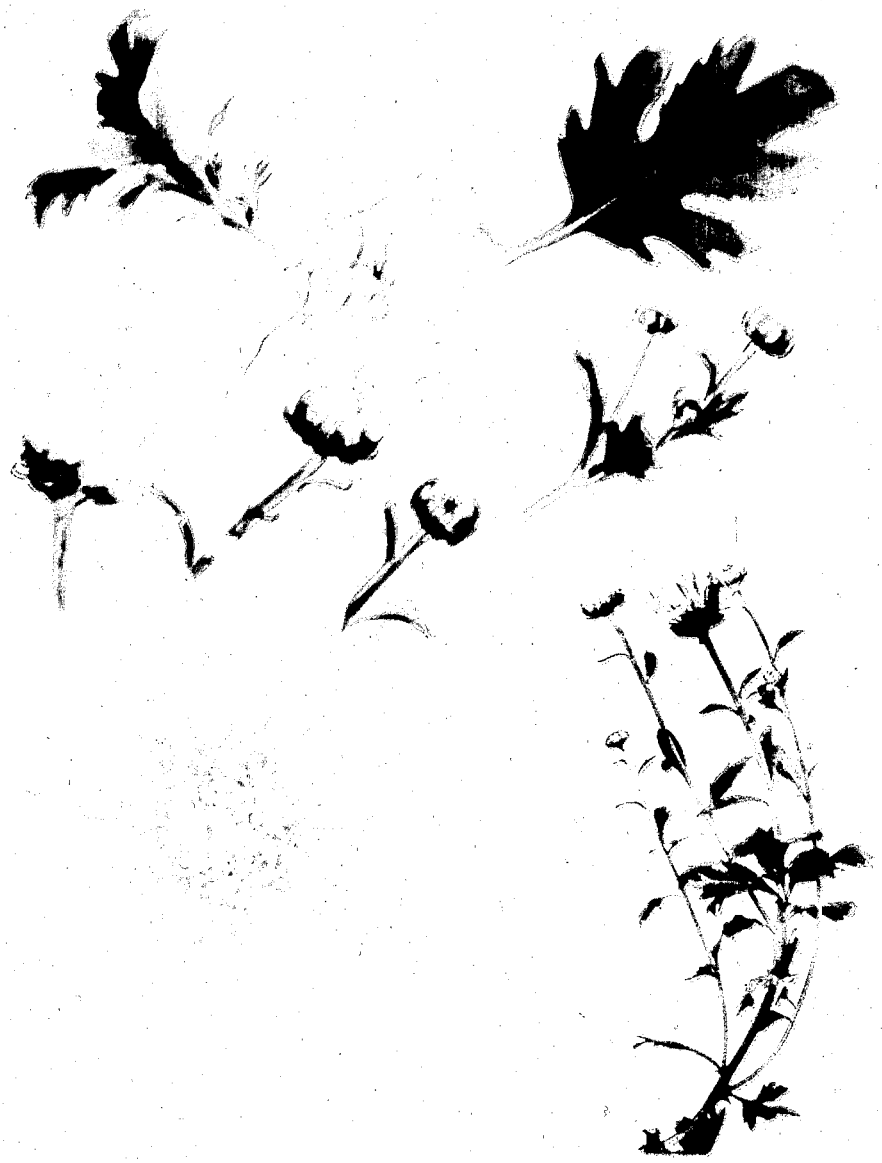
Inventor.
E. S. Boerner
By: Robb & Robb
Attorneys.

United States Patent Office

Plant Pat. 2,126
Patented Jan. 30, 1962

2,126
CHRYSANTHEMUM PLANT

Eugene S. Boerner, Newark, N.Y., assignor to Jackson & Perkins Company, Newark, N.Y., a corporation of New York Filed Mar. 17, 1961, Ser. No. 96,628
1 Claim. (Cl. 47—60)

The present invention relates to a new and distinct variety of chrysanthemum plant of the shaggy decorative class, which was originated by me by crossing an unnamed and unpatented seedling of the variety "W. F. Snyder" (unpatented) with the variety "Kingbird" (Plant Patent No. 1,306).

The primary objective of this breeding was to produce a new chrysanthemum variety which combines the earliness of the unnamed seedling parent, with the hardiness, bloom size and color of the parent variety "Kingbird." This objective was fully achieved, along with other desirable improvements, as evidenced by the following characteristics which are outstanding in the new variety and which distinguish it from its parents, as well as from all other varieties of which I am aware:

(1) An early blooming habit;
(2) A compact habit of growth;
(3) Good hardiness;
(4) Large flower size;
(5) Wide flower petals; and
(6) A distinctive and attractive general color tonality of the flowers corresponding to La France Pink, lightly overcast with Eosine Pink.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetable growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, in the early morning during the latter part of the month of October:

Parentage: Seedling.
*Seed parent.*—An unnamed seedling of "W. F. Snyder."
*Pollen parent.*—"Kingbird."
Classification: Shaggy decorative.

Growth: Free; compact.
Cold resistance: Winter hardy in northern New York State.
Blooming period: From September until frost.

*Flower*

Bud:
*Color.*—When sepals first divide—Massicot Yellow, Plate 16, lightly overcast with Spinel Pink, Plate 26 in the center of the petals. When petals begin to unfurl — Thulite Pink, Plate 26. When half-blown: inside of petals — Eosine Pink, Plate 1, with upper half of petals lightly overcast with Cartridge Buff, Plate 30; outside of petals — Eosine Pink, Plate 1, lightly overcast with La France Pink, Plate 1.
*Peduncle.*—Color—Bice Green, Plate 17. Strength—medium.

Bloom:
*Size.*—6½ inches.
*Stem.*—Medium strength.
*Form.*—Shaggy decorative.
*Petalage.*—Double.
*Color.*—Center of flower — Geranium Pink, Plate 1, lightly overcast with Eosine Pink, Plate 1. Outer petals — Ivory Yellow, Plate 30, lightly overcast with La France Pink, Plate 1. Base of petals — Chalcedony Yellow, Plate 17. Inside of petals — La France Pink, Plate 1, lightly overcast with Eosine Pink, Plate 1. Reverse of petals — La France Pink, Plate 1, lightly overcast with Hermosa Pink, Plate 1.
*Petals.*—Texture — soft. Form — wide; oval.
*Fragrance.*—Characteristic chrysanthemum.

*Plant*

Form: Bushy.
Growth: Full.
Foliage:
*Size.*—Medium.
*Quantity.*—Medium.
*Color.*—Upper side — Elm Green, Plate 1. Reverse side — Light Bice Green, Plate 17.
*Texture.*—Leathery.

I claim:

A new and distinct variety of chrysanthemum plant of the shaggy decorative class, substantially as herein shown and described, characterized particularly as to novelty by the unique combination of an early blooming habit, a compact habit of growth, good hardiness, large flower size, wide flower petals, and a distinctive and attractive general color tonality of the flowers corresponding to La France Pink, lightly overcast with Eosine Pink.

No references cited.